United States Patent

Cunningham

[11] Patent Number: 6,077,236
[45] Date of Patent: Jun. 20, 2000

[54] APPARATUS FOR MONITORING CARDIAC CONTRACTILITY

[76] Inventor: David Cunningham, Kinsale, Watt Road, Weir Bridge, Renfrewshire PA11 3DN, United Kingdom

[21] Appl. No.: 08/750,842
[22] PCT Filed: Jun. 7, 1994
[86] PCT No.: PCT/GB95/01326
  § 371 Date: Dec. 5, 1996
  § 102(e) Date: Dec. 5, 1996
[87] PCT Pub. No.: WO95/33517
  PCT Pub. Date: Dec. 14, 1995

[30] Foreign Application Priority Data

Jun. 7, 1994 [GB] United Kingdom .................. 9411397

[51] Int. Cl.[7] ......................................................... A61B 5/02
[52] U.S. Cl. ............................................. 600/587; 600/513
[58] Field of Search ..................................... 607/19, 17, 6; 600/513, 587

[56] References Cited

U.S. PATENT DOCUMENTS

| | | | |
|---|---|---|---|
| 5,304,208 | 4/1994 | Inguaggiato et al. | 607/17 |
| 5,425,750 | 6/1995 | Moberg | 607/17 |
| 5,480,412 | 1/1996 | Mouchawar et al. | 607/6 |
| 5,496,351 | 3/1996 | Plicchi et al. | 607/6 |

*Primary Examiner*—Kennedy J. Schaetzle

[57] ABSTRACT

Apparatus for monitoring cardiac contractility comprises a catheter having a tip for insertion into the ventricle of the heart muscle. At or proximate the tip is an acceleration transducer responsive to the natural, multi-directional heart acceleration to provide an acceleration signal to a signal processor. The apparatus is arranged to suppress frequencies outside the range approximately 15 Hz to approximately 100 Hz.

29 Claims, 13 Drawing Sheets

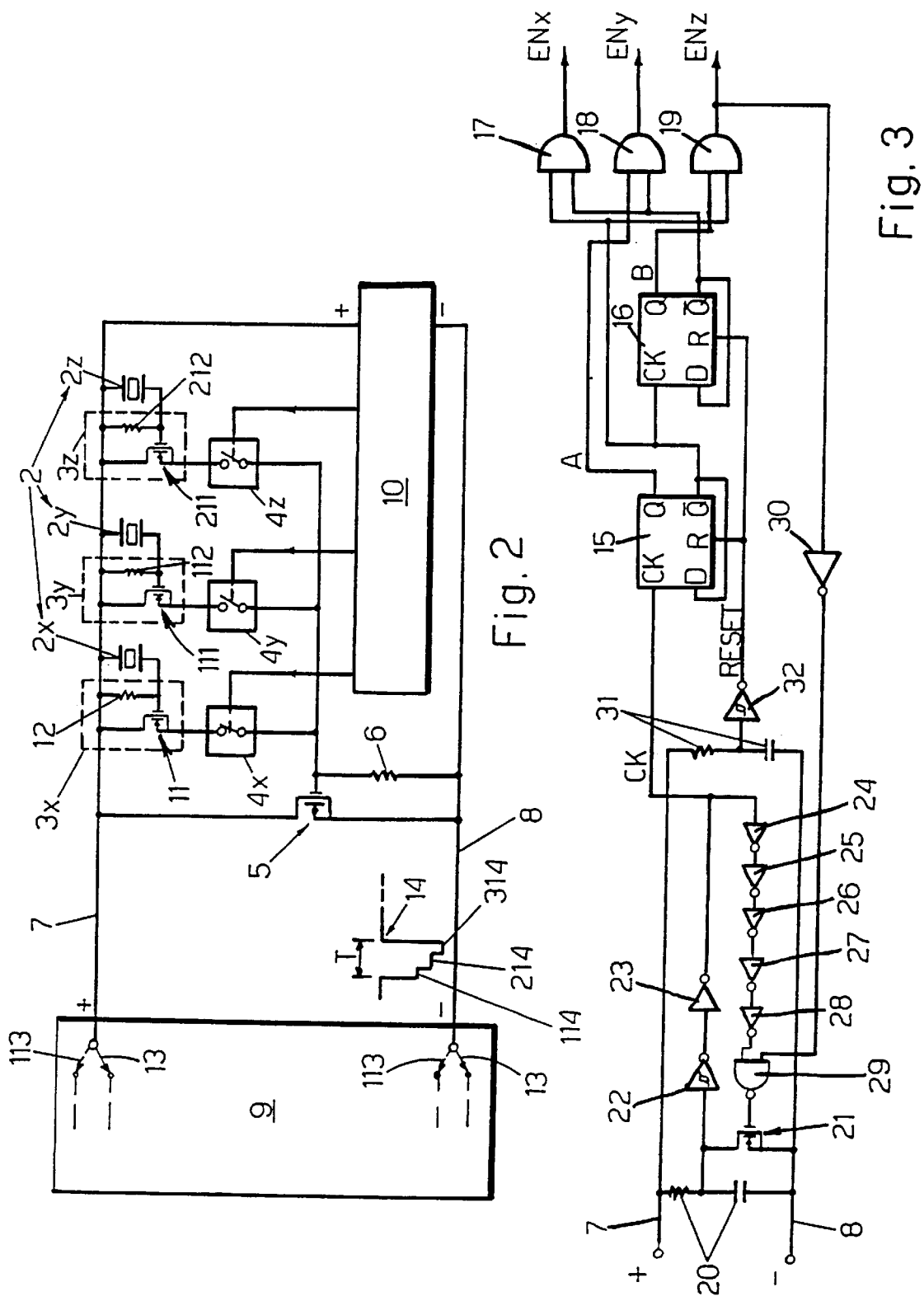

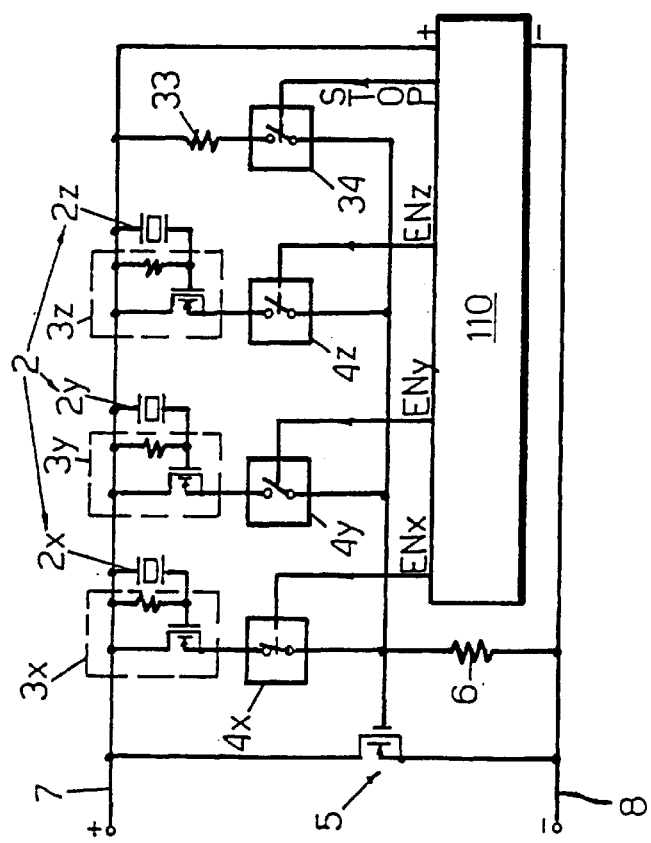
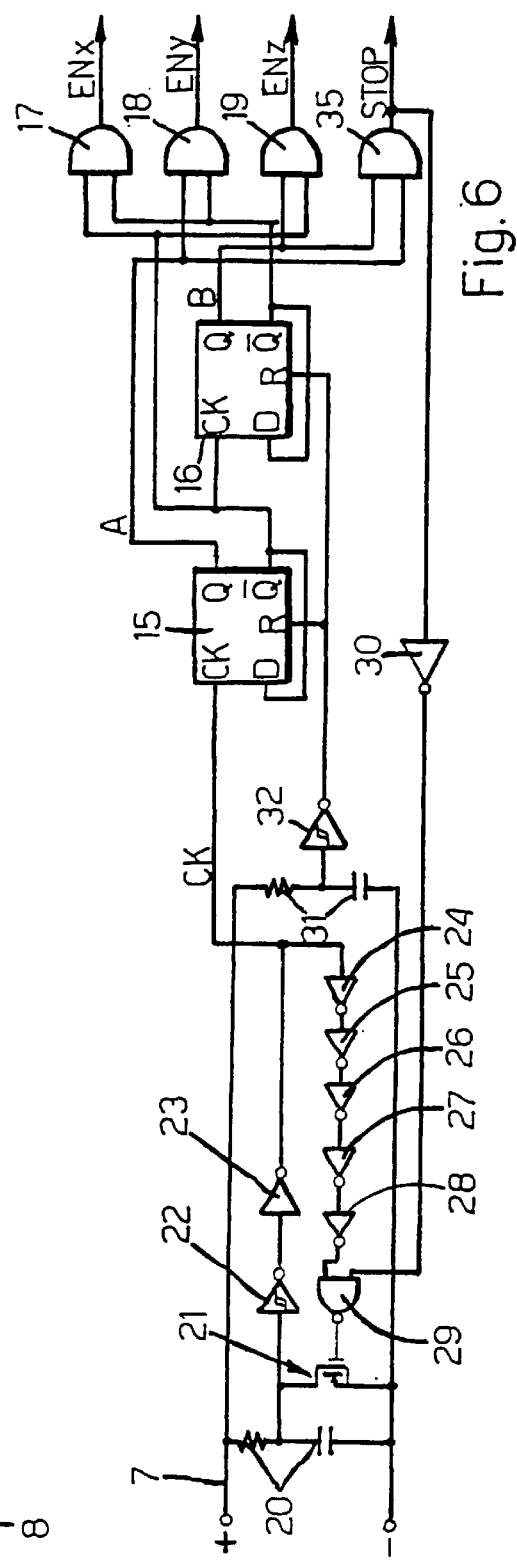
Fig. 5
Fig. 6

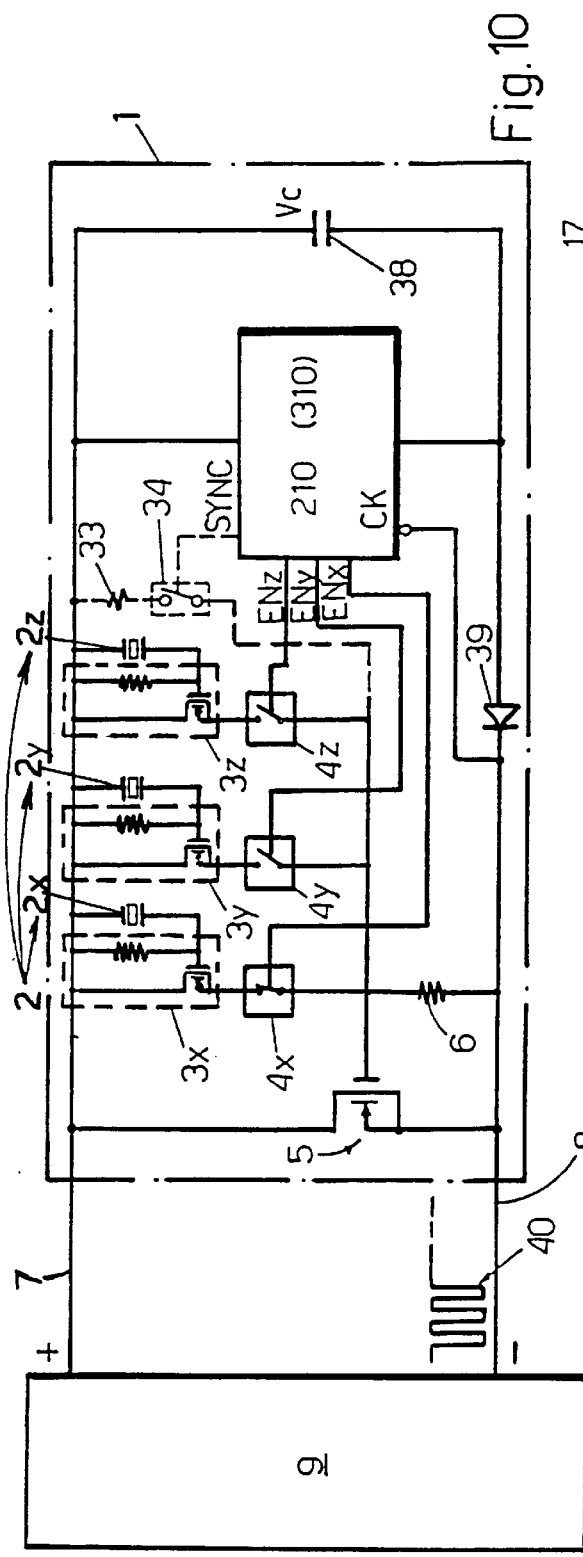
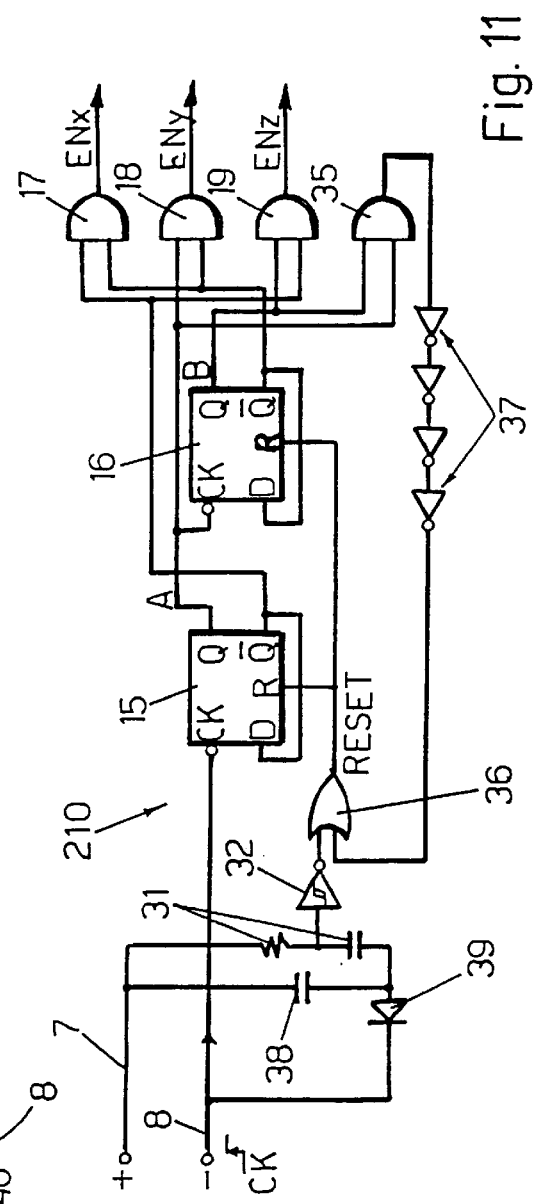
Fig. 10
Fig. 11

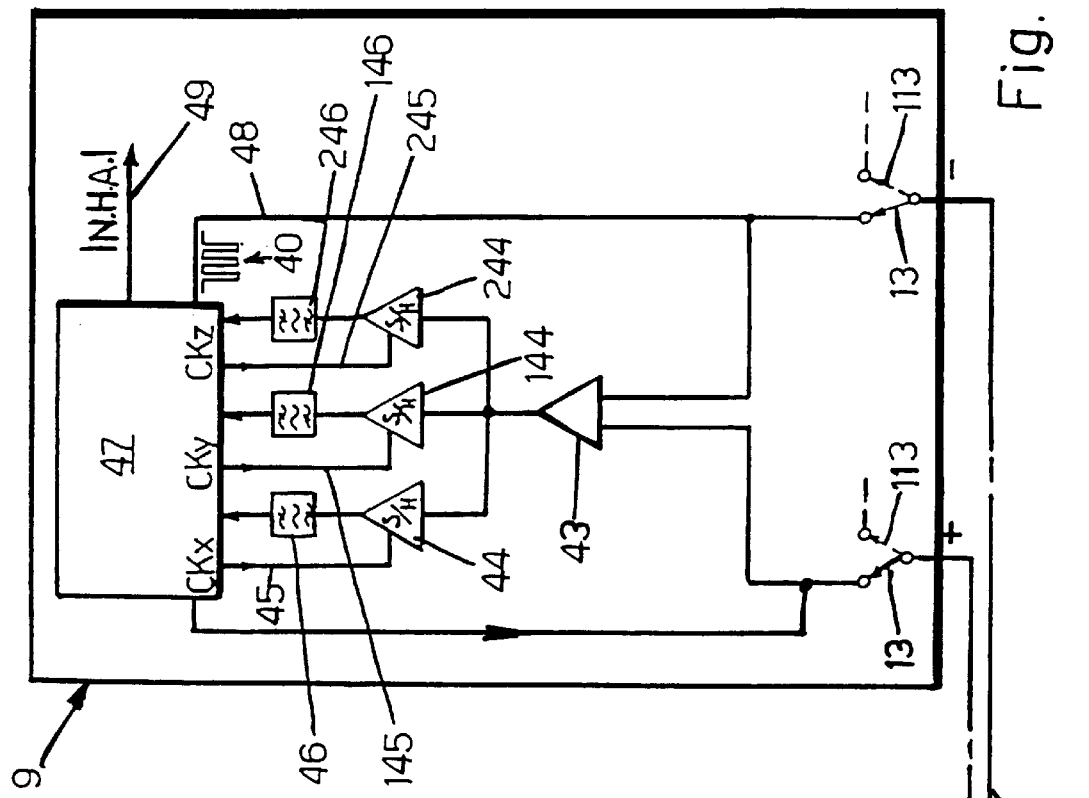
Fig. 15
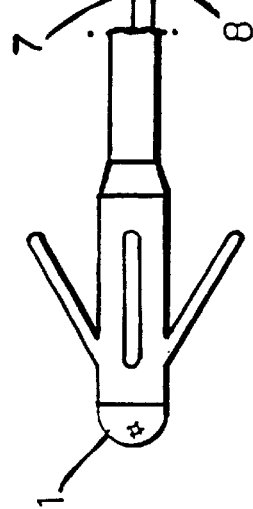
Fig. 16
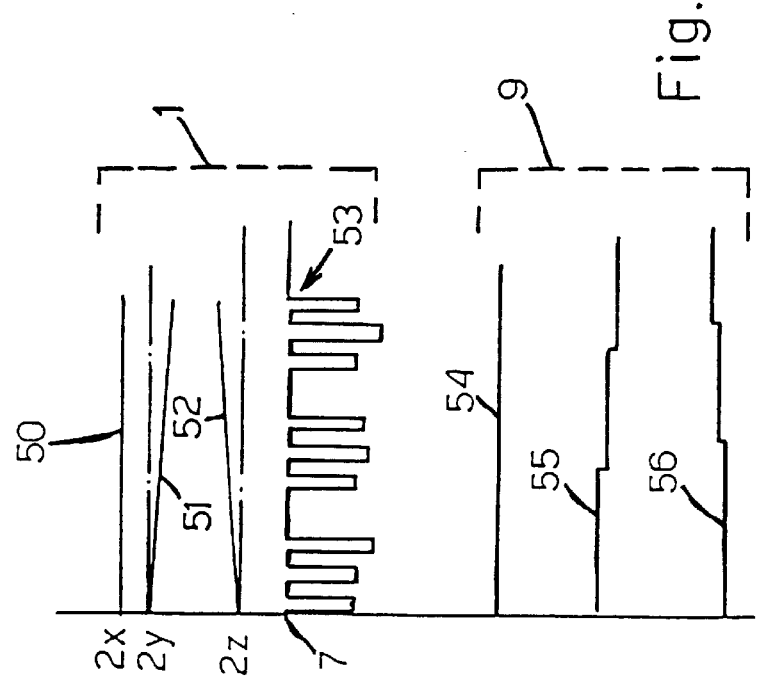

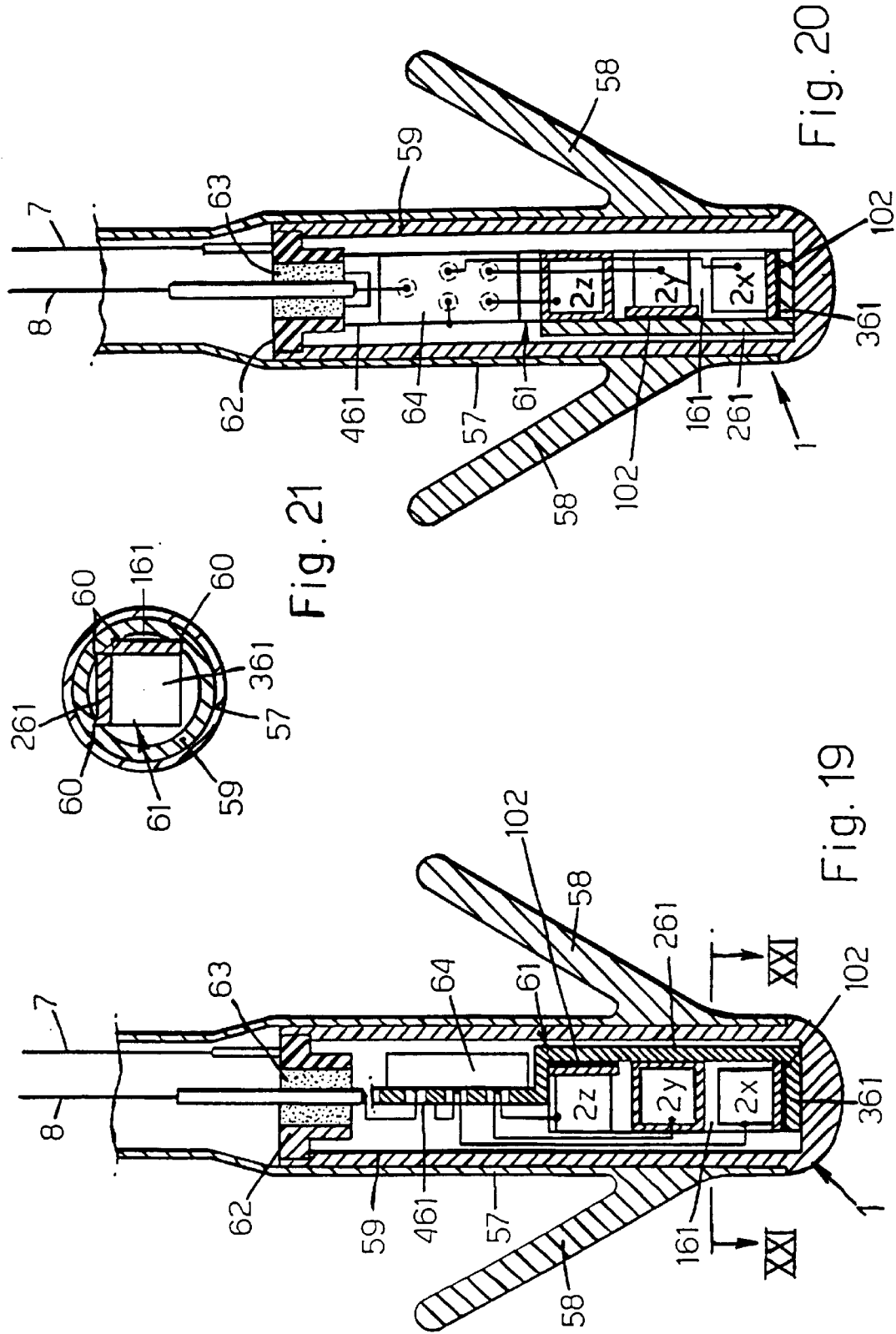

APPARATUS FOR MONITORING CARDIAC CONTRACTILITY

This application is a 371 application of PCT/GB95/01326, filed Jun. 7,1994.

This invention relates to apparatus for monitoring cardiac contractility. A Particular embodiment of the invention is suitable for application in pacemakers and in defibrillators, to permit the collection via telemetry of data relating to myocardial contractility and to monitor and control pharracological treatment, provided either by infusion or by conventional methods.

The use of accelerometers inserted in the heart by means of an intravascular catheter is known from French Pat. No. 2.224.752 of 9.4.73 held by Thomson medical Telco and from the publication "contractility studies using a catheter tip accelerometer in the left ventricle" by J. J. Schipper Heijn et al, in "International Conference on Biomedical Transducers", Nov. 7, 1975, Paris, France, which describes the acute and temporary application of the accelerometric device covered by the aforesaid French patent.

More recently, the publication "Characterisation of natural and total artificial heart acceleration" by Pantalos et al. in Vol. XXXV, Transactions of the American Society Artificial Internal Organs 1989, also described the application of an accelerometer to the epicardium of an animal's heart, to measure the variations in natural heart acceleration (NHA) due to the infusion of a drug which acts on the cardiovascular system.

Acceleration sensors have also already been used as sensors in an implantable system, and there are rate-responsive electronic stimulators whose control is based on the measurement of vibrations in the 3–70 Hz band, in Medtronic's Activitrax, or of vibrations below 8 Hz in CPI's Excel.

However, these sensors are disposed in the subcutaneous control unit, and are therefore sensitive only to vibrations and inertial forces transmitted through and to the whole body, and do not pick up the acceleration generated autonomously by the myocardium during the heart's operating cycle.

Application of endocardial acceleration in an implantable device is described in EP-A-0515319 of 12.05.92, "A cardiostimulator device of the rate responsive type" by Sorin Biomedica, which describes an electronic stimulator of the rate responsive type controlled by an acceleration sensor located in the tip of the electronic stimulation catheter, where the control signal is obtained by processing the measured acceleration component.

The invention is based on the realisation that the accelerometric system described in EP-A-0515319 does not allow the real endocardial acceleration to be measured properly during the cardiac cycle, for the following reasons:

a) The accelerometer measures the component of acceleration in one direction only, which in known devices normally corresponds to the longitudinal axis of the electrode which incorporates the acceleration sensor.

It has been shown in practice that it is totally impossible to orientate and keep orientated the axis of the electrode perpendicular to the part of the myocardial wall which is displaced rhythmically following the contraction of the heart. Consequently, the acceleration measured by the uniaxial sensor is related to the real acceleration by the cosine of the angle between the axis of the electrode and the direction of the cardiac acceleration vector. If this angle has a value of 90°, the corresponding cosine is zero, and therefore the value of any signal produced by the sensor will be equal to zero.

b) Research into heart kinetics has demonstrated that the displacement of the ventricle wall to which the electrode with the acceleration sensor is fixed is never unidirectional, but is expressed in ways which vary from one point to the next, generally as a complex vector which is given by the sum of the translatory and rotational components.

c) As described for example in Technical Note TN–008, Silicon Accelerometers, by IC Sensors-Eurosensor, the principle on which all uniaxial accelerometers are based may be reduced to the measurement of one component of the force in the specified direction exerted by a seismic mass subjected to the acceleration which is the subject of the measurement, where this force can be measured, as is known, with piezoresistive, piezoelectric, capacitive or other types of sensors. A rotation of 180° of the acceleration sensor with respect to a theoretical axis representing gravitational acceleration gives rise to an acceleration signal in the instrument varying from −1 G to +1 G, passing through zero when the direction of gravitational acceleration is perpendicular to the axis of greatest sensitivity of the sensor.

Since the principal values of acceleration of the resting heart are of the order of 1 G, and since, as stated previously, there are major multidirectional displacements of the whole cardiac body, and in particular of the apex of the ventricle in which the acceleration sensor is normally implanted, during the contraction of the heart muscle, it is possible that natural and instrumental effects may be superimposed to the extent that, in the limit case, they may cancel out or double the normal cardiac acceleration signal.

d) A further important reason why a uniaxial sensor is unsuitable not only for a determination of the absolute value of cardiac acceleration, as stated in paragraph a), but also in the real measurement of relative variations with respect to an initial base, consists in the fact, well known to physiologists and cardiologists, that the silhouette of the whole cardiac body and its cavities varies considerably within one heart, even in a few tenths of a second, and in ways varying from heart to heart and varying even in the same heart, according to its state of health, for example as a result of variations of what is known as the stroke volume. In practice, the silhouette of a heart changes rapidly during exertion and also changes over the long term and in relation to the clinical history of each person, in both the base and the exertion values.

It is therefore not reliable to use the signal of the uniaxial sensor even for the simple determination of relative variations of this value with respect to a base value, as occurs in any subject in the comparison between a resting state and the performance of an exercise test. The variation of the cardiac silhouette in the course of such a test certainly induces a variation of the angle between the direction of the acceleration and the axis of the sensor, so that any consideration of the variations relative to the measurement made becomes meaningless.

e) The heart silhouette also varies with the pressure exerted by the diaphragm on the heart, for example during variations of posture or during respiration. In the first case, the data obtained from a supine patient bear no relation to those from a standing patient. Respiration, however, causes unquantifiable rhythmic variation of the direction of the cardiac acceleration vector with respect to the axis of the unidirectional sensor, making the measurement correspondingly unreliable.

The considerations set out above fully demonstrate the serious limitations of a system with a uniaxial acceleration sensor such as that described in EPA 0515319, and experiments which have been conducted have confirmed that the differences between the various axial components of endocardial acceleration may be significant.

Against this background, in accordance with one aspect of the invention, there is provided apparatus for monitoring cardiac contractility, comprising a catheter having a tip for insertion into the ventricle of the heart muscle, said catheter containing at or proximate its tip an acceleration transducer responsive to the natural heart acceleration to provide an acceleration signal via said catheter to signal processing means, wherein the acceleration transducer is responsive to acceleration in any spatial direction.

Further consideration should be given to the method of processing of the uniaxial acceleration sensor signal which is provided in EPA 0515319, where among other things it is specified that the peak value or mean value of the NHA signal may be identified.

It is important to point out that, according to the text and graphs reproduced in the paper by Pantalos and in the previously mentioned EPA 0515319, there is no limitation on the inherent frequency band of the sensor, which operates typically at minimum frequencies of zero or a few fractions of 1 Hz, depending on whether the transducer used is of the piezoresistive or piezoelectric type, and with a maximum frequency of up to approximately 25 kHz as described by Pantalos. From experiments conducted and from data collected by the applicant, it was found that the peak NHA value of the signal obtained without any specific band limitation is dependent on and governed by physiological phenomena which differed completely in relation to the specific anatomical configuration of the heart and its state of contraction. The low-frequency component of the said signal, lying approximately between zero and 15 Hz, is significantly affected by the movement of the part of the heart on which the measurement is being made, owing to the combined effect of the displacement of the endocardial walls which participate in the contraction and in the total movement of the cardiac body, as a reaction to the ejection phase, as a variation due to a change in posture or to respiration, and as an effect combined with other mechanical influences on the whole cardiac body.

From experiments conducted by the applicant, it was found that only the component of the NHA signal within the band of approximately 15–100 Hz had a peak which always coincided with the isovolunetric phase of cardiac contraction, when the heart was macroscopically immobile, and therefore the maximum amplitude of the accelerometer signal in this frequency range necessarily and uniquely described the vibratory phenomenon indicating the state of contraction of the heart. Before executing ventricular ejection, the myocardium brings its muscle fibres into tension, and these then shorten during the said ejection phase, so that the maximum amplitude of the vibrations in the range of approximately 15–100 Hz represents the potential contractile capacity of the heart.

From the experiments conducted by the applicant, it was found that the band above 100 Hz may also be a source of errors since, during the phases of ejection and of opening and closing of the heart valves, signals at frequencies above 100 Hz may sometimes occur, depending solely on the flow dynamics and on the valve dynamics, and that their amplitude may be far greater than that of the vibrations generated in the isovolumetric contraction phase.

Against this background, in accordance with a second aspect of the invention there is provided apparatus for monitoring cardiac contractility, comprising a catheter having a tip for insertion into the ventricle of the heart muscle, said catheter containing at or proximate its tip an acceleration transducer responsive to the natural heart acceleration to provide an acceleration signal via said catheter to signal processing means, wherein the signal processing means and/or the acceleration transducer is or are arranged to suppress frequencies outside the range approximately 15 Hz to approximately 100 Hz.

Two examples of rultiaxial transducers will be described. A first multiaxial transducer comprises an assembly of three uniaxial acceleration transducers. Each has an upper band limit which for mechanical reasons is limited to approximately 100 Hz. The transducers are orientated perpendicularly to each other and located in the tip of the catheter where there is also mounted an integrated electronic circuit enabling a master control unit to receive the three signals of the transducers in successive time intervals. A time interval of the order of approximately 100 microseconds is used, in a ratio of $\frac{1}{30}$ to the sampling period which is typically approximately 3000 microseconds. This method of operation enables the estimated consumption of approximately 30 $\mu$A in the 100 microseconds of sampling to be decreased to a mean consumption of approximately 1 $\mu$A which is fully compatible with the present criteria of implantability. The data are transmitted along the catheter with a two-wire conductor of simple form. By using only $\frac{1}{30}$ of the previously mentioned time for sampling, it is possible to use the said conductors and the catheter tip for any necessary functions of sensing electrophysiological signals, electrical stimulation, defibrillation, or other.

The second example of meultiaxial transducer constitutes a third aspect of the invention. Broadly, in accordance with the third aspect of the invention there is provided an acceleration transducer, comprising: a casing of piezoelectric or piezoresistive material provided on inner and outer surfaces with respective conductive coatings, the inner conductive coating being connected to an external contact which is electrically isolated from the outer conductive coating, and a seismic mass being provided inside the said casing body. A preferred embodiment of this transducer overcomes by mechanical means the problem of providing a signal dependent on acceleration, regardless of its direction, by using a transducer comprising two linked hemispherical caps within which is disposed a seismic mass of spherical form. The hemispherical caps are made of materials which exhibit the phenomenon of piezoelectricity when they are stressed radially by the seismic mass. Regardless of the direction of the inertial stress, the seismic mass will stress the caps of the transducer which will produce an electrical signal proportional to the stress. The electronic circuitry disposed in the tip of the catheter and associated with the said multiaxial accelerometer can be limited in this case to a simple impedance matching circuit which, when commanded by the master control unit, is activated for approximately 30 microseconds once every 3000 microseconds, permitting a significant reduction in current consumption, which will not exceed approximately 0.3 $\mu$A. The link from the transducer and its associated electronic circuit to the master control unit is a two-wire link and permits alternation between the phases of sampling of the accelerometer and those of sensing, pacing and defibrillation.

In this case also, the accelerometer may be. characterized by a band limited mechanically at the top end to 100 Hz; otherwise, owing to the limited operating consumption mentioned previously, the signal picked up by the transducer without any mechanical band limitation, may be reconstructed accurately with an appropriate sampling frequency, for example of the order of approximately 1000 Hz, and the reconstructed signal can then be electronically filtered in the band of approximately 15–100 Hz, for the extraction of that part of the signal which represents cardiac contractility in the isovolumetric phase.

Embodiments of the invention will now be described by way of example with reference to the accompanying drawings, in which:

FIG. 2 shows in greater detail the electronic circuit shown in FIG. 1;

FIG. 3 shows in detail the timing circuit of the electronic circuit in the preceding figures;

FIG. 5 shows an electronic circuit of a second embodiment of the device;

FIG. 6 shows in detail the timing circuit of the circuit in FIG. 5;

FIG. 10 shows the electronic circuit of a further embodiment of the device;

FIG. 11 shows in detail the timing circuit of the electronic circuit in FIG. 10;

FIG. 15 is a block diagram of the part of the electronic circuit disposed in the subcutaneously implanted master control unit, designed for the collection and processing of the signals from the multiaxial transducer as shown in the preceding figures;

FIG. 16 shows the forms of certain signals, some originating from the tip of the implanted catheter and some reconstructed in the master control unit;

FIGS. 19 and 20 are longitudinal sections, viewed from two points separated by an angle of 90° through the hollow metal point (tip) of an implantable catheter containing the device, according to any one of the versions illustrated in the preceding figures;

FIG. 21 shows further details of the catheter point as shown in FIG. 19, in transverse section along the line XXI—XXI;

Figure 1:
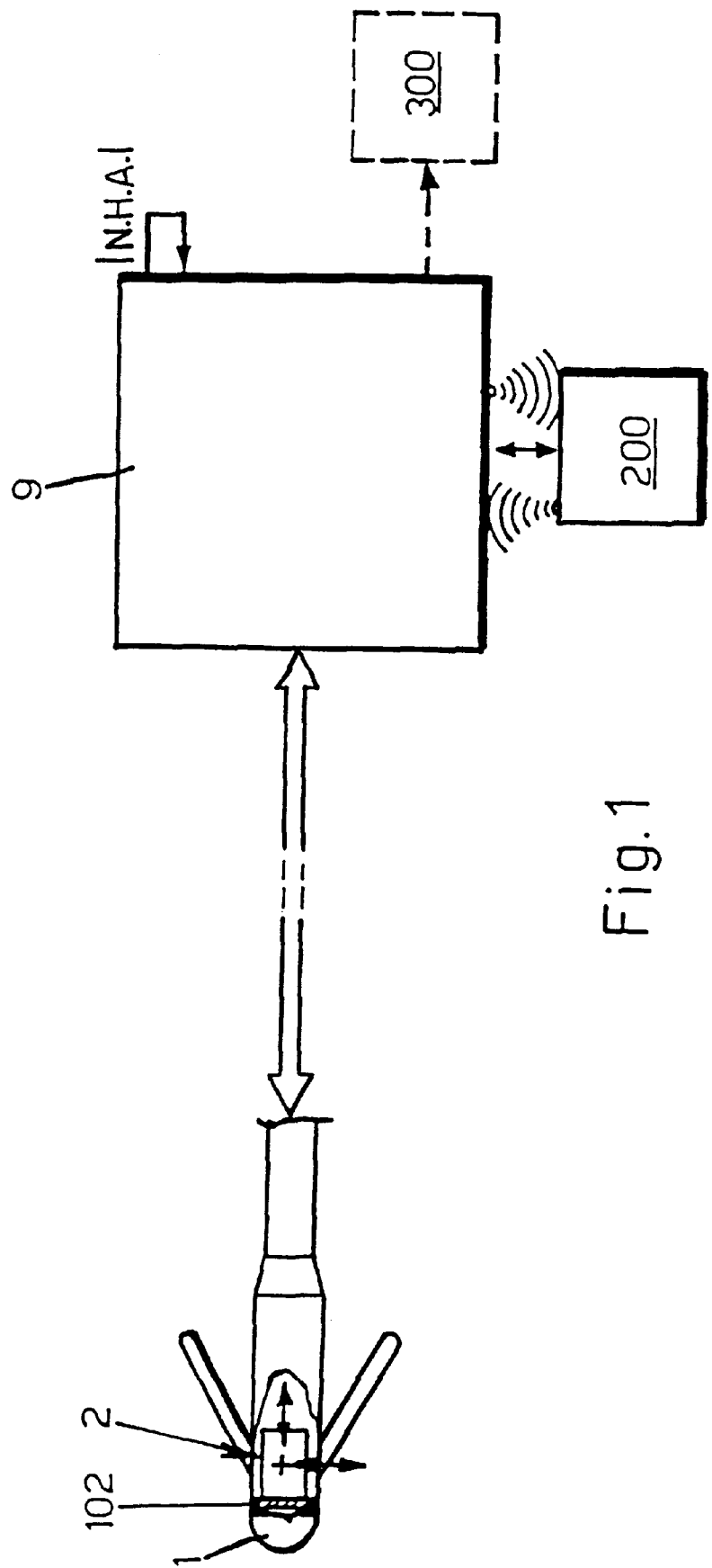
FIG. 1 is a block diagram of an implantable device embodying to the invention.

Referring to FIG. 1 a subcutaneous master control unit 9, is connected to a multiaxial acceleration transducer 2 located in the tip 1 of the catheter implanted in the heart, with the interposition of a mechanical damper 102 which mechanically limits to approximately 100 Hz the upper limit of the response frequency of the said acceleration transducer, in order to avoid significant sources of error. The master control unit 9 acts as an interface with the multiaxial acceleration transducer 2 and processes the acceleration signal to calculate the cardiac contractility in each cardiac cycle, within a frequency band between 15–100 Hz approximately, which also enables significant sources of error to be excluded. The master control unit 9 also acts as an interface, via bidirectional telemetry, with external monitoring and control devices 200, which permit the use of the said master control unit and the associated implantable device with the multiaxial acceleration transducer for any necessary electrical stimulation or defibrillation functions, or for monitoring the operation of implantable or external devices 300 used for infusion of drugs, which also have to operate, in association with other parameters if necessary, in relation to the measured values of cardiac contractility.

According to a simpler embodiment, the system may be limited to the transmission to the outside of the cardiac contractility detected by the multiaxial acceleration transducer. The use of bidirectional telemetry systems for monitoring and control of the non-invasive programming of all the functions of the system is also envisaged.

FIG. 2 shows that, according to a first embodiment of the invention, there is fixed in the tip 1 of the catheter an acceleration transducer of the triaxial type, formed by three uniaxial transducers 2x-2y-2z with an upper frequency limit mechanically limited to approximately 100 Hz, as stated previously, and perpendicular to each other, one of which is, for example, orientated along the axis of the catheter (see below). For this purpose it would be possible, for example, to use a triaxial piezoelectric transducer such as the Endevco Model 23 Picotriax Accelerometer, made with dimensions suitable for the purpose, or a piezoresistive triaxial transducer such as the Entran EGA3 made by Entran, also made with suitable dimensions by micromachining techniques. The transducers are associated with corresponding connection and amplification means 3x-3y-3z and with corresponding switches 4x-4y-4z whose outputs are connected to the gate of a MOS transistor 5 which acts as an output buffer. The number 6 indicates the load resistance of the devices 3x-3y-3z, while 7 and 8 indicate the electrically insulated wires which run inside the catheter and connect the components of the device in question, disposed inside the catheter, to the subcutaneously implanted master control unit 9.

The circuit 10 branched from the buffer 5 and fitted in the tip 1 of the catheter performs timing functions, to make available in the single output conductor 8 the signals from the three uniaxial transducers 2x-2y-2z in distinct and successive time intervals. The master control unit 9 reconstructs within itself the three analog signals from the three acceleration transducers activated in a pulsed mode, amplifies them, filters them in a band from 15 to 100 Hz approximately, and measures within each cardiac cycle the peak-to-peak value of acceleration in the three directions considered, namely x-y-z. By filtering the three analog signals it is possible to select the cardiac vibrations characterising the isovolunetric pre-ejection phase. The master control unit 9 then calculates the modulus of the three peak-to-peak values of acceleration relative to the cardiac cycle concerned, according to the following relation:

$$|NHA|pp = \sqrt{(NHApp)^2 x + (NHApp)^2 y + (NHApp)^2 z}$$

or calculates the mean value of the three peak-to-peak peak values of acceleration relative to the same cardiac cycle, according to the relation:

$$\overline{NHA}\ pp = \frac{(NHApp)x + (NHApp)y + (NHApp)z}{3}$$

These parameters are taken as representative of the contractile state of the heart in the cycle concerned.

In the following description, as in the drawings, reference is frequently made for simplicity's sake to the modulus of the NHA only, although it should be understood that the alternative use of the mean value or of any other processing of the signals from the three acceleration transducers for each cardiac cycle also lies within the scope of protection of the present invention.

Operations of the type stated above may be performed by suitably combining linear, logarithmic, and antilogarithmic amplifiers, or by means of digital calculation algorithms, with techniques known well to those skilled in the art.

The object of implantability which, for example in the context of a pacemaker of the rate-responsive type, may be expressed as the availability of the catheter for any necessary functions of sensing and stimulation, requires the limitation of the percentage of time in which the conductors 7 and 8 are used for the measurement and transmission of the signals read by the multiaxial acceleration transducer.

Given that the time interval between consecutive readings of the acceleration transducers produced by the transducers 2x-2y-2z will be of the order of 3000 microseconds, corresponding to a signal sampling frequency of approximately 330 Hz, suitable for frequency content of the event which is to be analysed, and given that, as already stated in the introduction of the present disclosure, the requirement of implantability necessitates basic consumption of the system within the range 1–5 $\mu$A, including the general consumption of the master control unit 9 and not only that necessary for the collection of the signals from the transducers, it will be understood that a mean consumption of not more than 2 $\mu$A must be allocated to this function.

Since, in the present state of the technology, the activation of an MOS buffer which provides a low impedance of the signals transmitted along the catheter may require a current of the order of 30 $\mu$A and since, as in the present technology of implantable catheters which use a miniature coaxial or parallel wire lead with parasitic capacitances of the order of tens of picoFarads, for example of the order of 50 pF, it may be deduced from the equation I=C.dV/dt that, assuming that C has the previously mentioned value of 50 pF, the current I has the specified value of 30 $\mu$A and the operating voltage V of the electronic components disposed in the tip 1 has the characteristic value of 2 volts, the delay in the switch-on of these components will be of the order of approximately 3.3 microseconds.

Consequently, especially when modern multispiral catheters are used, the minimum time which is reasonably sufficient to activate a transducer and read the corresponding data is of the order of 30 microseconds, while in the present case, owing to the presence of three uniaxial transducers 2x-2y-2z, activation for a total of approximately 90–100 microseconds is necessary, for each sampling, to permit the data from the three transducers to be available in succession.

Since the duty cycle will be of the order of 1/30 for a repetition period of 3000 microseconds, the mean consumption is of the order of 1 $\mu$A which is a necessary and sufficient condition for the implantability of the device. This example is valid in cases where the transducers are operated by battery power. However, even when duplicated battery power is used, the basic consumption will never exceed 2 $\mu$A and will therefore be compatible with the characteristics of implantability of the instrument.

According to the basic concept resulting from all the above considerations, approximately 100 microseconds of each sampling cycle must be dedicated to the reading of signals from the three acceleration transducers 2x-2y-2z.

The processing of these signals by the master control unit 9 makes it necessary to distinguish them within the interval in question. The methods which may be used for this purpose and which are compatible with the previously defined characteristics of implantability require that the complexity of the electronic circuitry to be disposed within the tip 1 of the catheter be kept to a minimum, unlike that of the said unit 9 which has fewer physical and mechanical limitations.

Consequently, while maintaining the principle that only a small time interval of the available cycle will be dedicated to the analysis of the signal from the transducers 2x-2y-2z, some possible non-restrictive solutions for the realisation of the instrument shown in FIG. 1 will now be considered in more detail.

FIG. 2 shows that the uniaxial transducers 2x-2y-2z, assumed to be of the piezoelectric type, are associated with a buffer consisting of MOS transistors 11-111-211 with corresponding polarising resistors 12-112-212 which convert the electrical charge generated by the piezoelectric element into a voltage readable between the drain and source of each of the said components.

Assuming that 7 is the positive reference electrode supplying the transducers and the corresponding timing circuit 10, the subcutaneous unit 9 changes from the PACING/SENSING state indicated by 113 to the SENSORS state indicated by 13, for the measurement of the modulus or of the mean of the NHA values read from the three transducers within the cardiac cycle in question, relative to the 15–100 Hz, and sends a constant-current pulse which enables the circuit 10 to come into operation with a limited delay of the order of a microsecond and for a time interval indicated by T in the waveform 14. It should be understood that the stepped waveform indicated by 14 is purely an example and is not restrictive, and that the waveform may therefore be of any type, for example consisting of rising instead of descending steps, or by an alternation of rising and descending steps or descending and rising steps, according to the signals generated by the transducers and by the operating thresholds of the transistors 11-111-211.

The timing circuit 10 has no effect at all on the output voltage present on the negative electrode 8, since most of the excitation current of the whole circuit disposed in the tip of the catheter flows in the buffer 5 which determines its source voltage on the basis of its gate voltage, which in turn is determined by the buffered output of the individual transducers 2x-2y-2z, activated individually at different times.

Current absorption by the circuit 10, in the case of a typical C-MOS device, occurs in particular only in the instants of switching from one transducer to the next, in other words in the initial transient of the activation pulse of each individual transducer, while during the 30 microseconds of data reading by the master control unit 9 following the said transient the timing circuit is in a static state and consequently has absolutely no effect on the voltage measurable at the drain and source terminals of the buffer 5. It should also be noted that the transistor 5 is a device with low output impedance and therefore is not affected in any way even by current consumptions of the order of microamperes which may relate to the time constant 20 for the generation of the clock pulse, if a current of the order of 30 $\mu$A flows in it.

Assuming that current pulses of the order of 30 $\mu$A are used with intervals of T/3=30 microseconds, the subcutaneous unit 9 must supply the said current pulses with a duration of T=90 (approximately 100) microseconds.

For example, when an NHA signal at 330 Hz is sampled, the repetition period or time interval between two successive activations of the timing circuit 10 is approximately 3 milliseconds, with a mean consumption of approximately one microampere, perfectly compatible with an implantable device. It should also be emphasised that the sampling of the three signals in different time intervals has no effect at all on the simultaneity of the three events detected, since the three samplings are performed within a time slot T of the order of 100 microseconds and the dynamic of the signals in question is not of a type which induces variations in the signals in this time interval.

Figure 4:
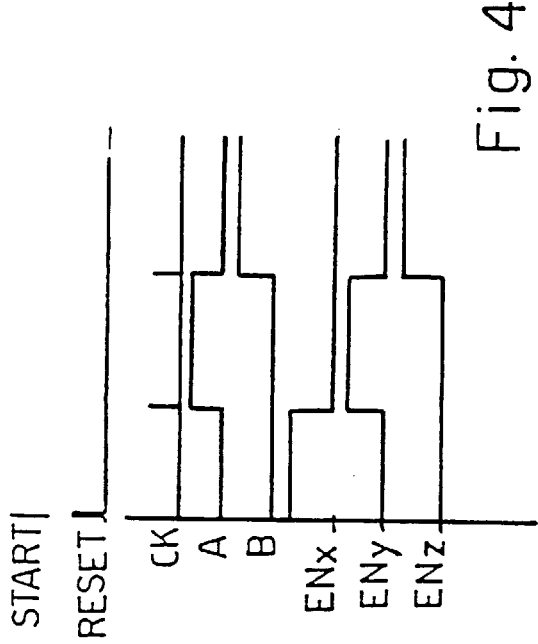
FIG. 4 shows the forms of the output signals from some significant components of the circuit shown in FIG. 3.

FIG. 3 shows a possible embodiment of the timing circuit 10. The numbers 15 and 16 indicate two D-type flip-flops having their D inputs connected to the $\overline{Q}$ output and having their Q and $\overline{Q}$ outputs controlling the switches 4x-4y-4z through the corresponding AND-type decoding logic circuits 17-18-19. ENx-ENy-ENz indicate the outputs of the said logic circuits. The time constant 20, the transistor 21, the Schmitt trigger 22 and the inverter 23, with the delay line formed by the series of inverters 24-25-26-27-28 and the NAND logic circuit 29, provide the clock pulses CK required for the operation of the counter formed by units 15 and 16. If it is necessary to use a time slot of 90 microseconds, as stated above, the tire constant 20 will be such that it provides clock pulses at intervals of 30 microseconds, as indicated in the waveform in FIG. 4, where A and B represent the signals present at the outputs Q of the units 15 and 16. When the ENz output of the AND logic 19 goes high, the output of the NAND logic 29 is set high through the inverter 30, the clock pulse CK is interrupted and the operation of the timing circuit 10 is stopped. The time constant 31 may for example be of the order of a microsecond, and it is passed through the Schmitt trigger 32 to the input R of the units 15-16 to reset them when the circuit is switched on.

The master control unit 9, with reference to the start of the procedure which it controls, proceeds to read at suitable time intervals the two-wire output 7-8 of the catheter, to collect the data relating to the transducers 2x-2y-2z.

Figure 9:
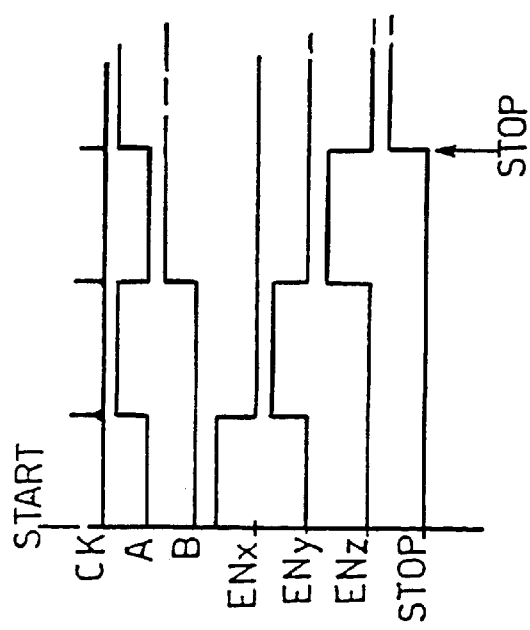
FIG. 9 shows the form of the output signals from some significant components of the circuit shown in FIG. 6.

To prevent desynchronisation phenomena between the reading of the master control unit 9 and the output phases of the accelerometer signals generated autonomously by the timing circuit 10, it is possible to make the said master control unit 9 self-adjusting to the timing of the timing circuit, for example by the solution described below with reference to FIG. 5. A resistive load 33 with known characteristics is branched from the acceleration transducers, and consists of a resistor or a MOS transistor network, and a switch 34, controlled by the said timing circuit 110 controlling the transducer switches 4x-4y-4z, is provided and will be described below. The possible embodiment of the timing circuit 110 is illustrated in FIG. 6 and differs from the solution in FIG. 3 by the presence of a specific AND logic 35 which activates a fourth state of the circuit following the transducers. The signals of the significant components of the circuit 110 in FIG. 6 are illustrated in FIG. 9.

At the moment when the master control unit 9 energises the timing circuit 110, the latter behaves as the preceding circuit shown in FIG. 3 in respect of the sequential activation of the three acceleration transducers 2x-2y-2z, the difference being that after the interval of activation of the last transducer 2z the switch 34 is closed, while all the switches 4x-4y-4z are open, so that the voltage present at the negative pole of the output buffer 5 is determined by the loads 6 and 33. By establishing a suitable ratio between these two loads, it is possible to make the voltage present on the negative pole of the buffer 5, at the moment of closing of the switch 34, very different from that in the intermediate states of sequential activation of the three acceleration transducers. For example, if the three buffers 11-111-211 associated with the acceleration transducers were characterized by conduction thresholds of the order of one volt, and if the output buffer 5 had a threshold also of the order of one volt, the voltage read at the terminals of the output buffer during the activation of the three acceleration transducers, disregarding small variations superimposed on it due to the signals generated by the transducers themselves, would be of the order of two volts. By suitably setting the ratio between the loads 33 and 6, it is possible to make the voltage read at the terminals of the output buffer 5 in the said final state to be of the order of three volts. By means of a comparator or other means known to those skilled in the art and not illustrated, the master control unit 9 would thus be enabled to recognise the said final state without difficulty and to register the termination of NHA measurement, and could therefore proceed to interrupt the current which had been supplied to the circuit located in the tip of the catheter.

Figure 7:
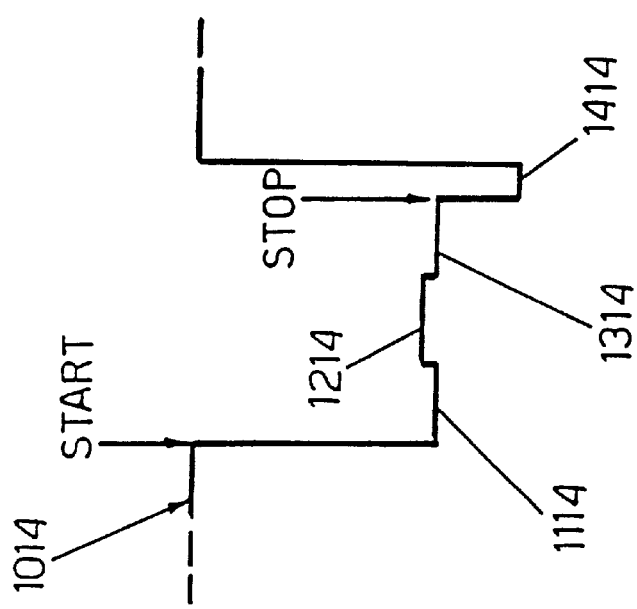

By way of example, FIG. 7 shows the waveform 1014 which the master control unit 9 perceives during each activation cycle of the timing circuit 110. The steps 1114-1214-1314 relate to the activation of the three acceleration transducers, while the final step 1414 relates to the final state of closure of the switch 34.

The master control unit 9 is aware of the instant of the start of measurement, since it is this unit that determines it; and since, as stated previously, the instant of the end of the enabling cycle of the three acceleration transducers is also known, it can calculate the total time T required to make the measurements on the particular catheter in question and can assign to each transducer a reading time of ⅓ T. The master control unit 9 can perform this test operation periodically, at programmed time intervals and in a totally autonomous way in all cases.

The power consumption of the device does not undergo large variations, since the introduced fourth state lasts only for as long as is necessary for the master control unit to recognise it. The final state may be such that it generates a voltage which saturates the current generator disposed in the master control unit 9 and which supplies the device inside the tip of the catheter. In this situation, the power consumption corresponding to the final stable state would be much less than that in the phases of activation of the acceleration transducers.

Figure 8:
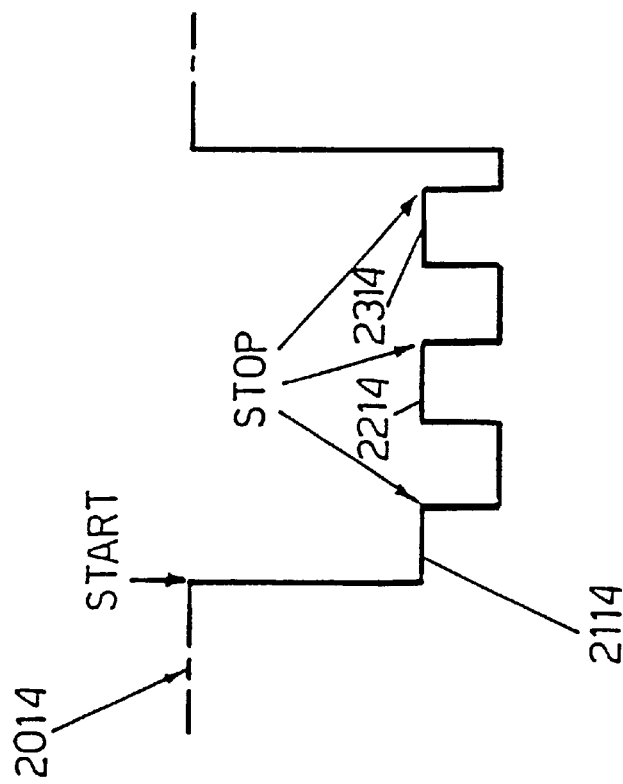
FIGS. 7 and 8 show the possible forms of the cyclic activation signal of the device as shown in FIGS. 5 and 6.

By slightly increasing the complexity of the delay logic, without altering in any way the dimensions of the integrated circuit located in the tip of the catheter, it is possible to generate a STOP signal after the activation of each transducer, for example as illustrated in the waveform indicated by 2014 in FIG. 8, where the components 2114-2214-2314 relate to the activation of the three transducers, while the low components relate to the STOP signals.

Another method of attaining the desired objective consists in providing in the master control unit 9 means which activate the reading of each acceleration transducer by three successive pulses spaced apart by 30 microseconds, which activate inside the tip of the catheter a decoding output counter which acts as a timing circuit and permits the sequential reading of the signals. This circuit uses, as switching clock pulses, the activation pulses from the master control unit 9, and the control of data collection is thus totally assigned to the said master control unit, the internal circuitry of the tip 1 of the catheter being used to switch the three transducers sequentially according to the three activation pulses sent in succession from the master control unit 9.

Figure 13:
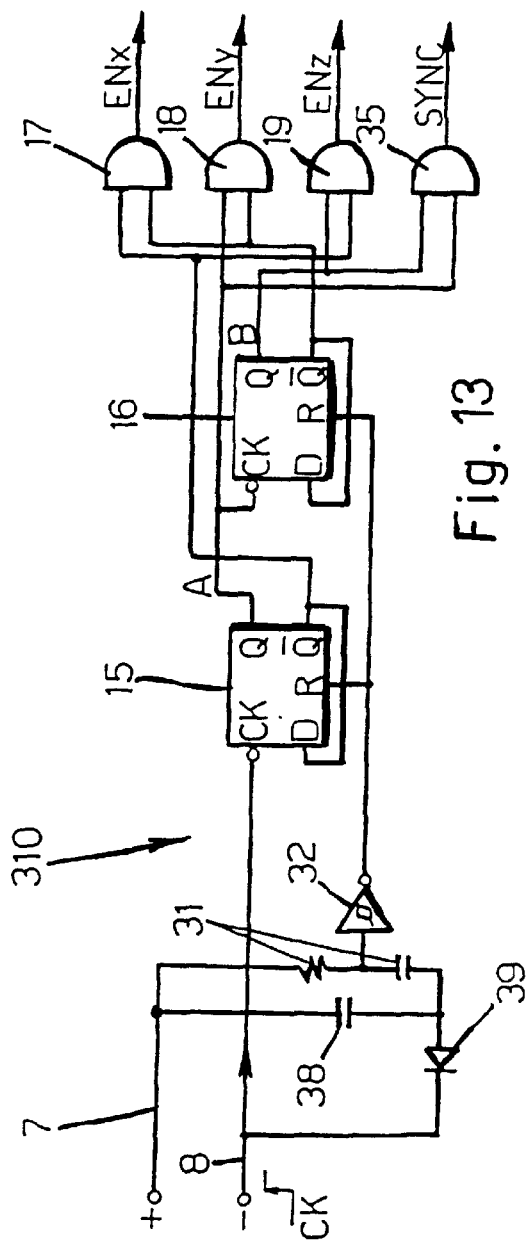
FIG. 13 shows a different embodiment of the timing circuit of the electronic circuit shown in FIG. 10, including the final synchronisation stage indicated in broken lines.

FIG. 10 is a block diagram of a solution of this type which differs from that shown in FIG. 5 in the provision of a three-state timing circuit 210 or a four-state circuit 310, as shown in the detail of FIGS. 11 and 13, both without an internal clock.

The solution shown in FIG. 11, which illustrates the three-state timing circuit 210, without components 33 and 34 shown in FIG. 10, differs from that in FIG. 6 in the absence of an autonomous clock circuit. The OR logic 36, with the AND logic 35 and the delay line 37 consisting simply of a sequence of inverters, make it possible to avoid the state A=B=1 which is not used in this case. The other input of the logic circuit 36 is connected to the Schmitt trigger 32 associated with the time constant 31 and the output of the said logic circuit 36 is connected to the reset R of units 15 and 16. The clock input CK of unit 15 is then negated to permit switching at the start of each activation pulse, and is connected directly to terminal 8, while the CK input of unit 16 is also negated and is connected to the output Q of the unit 15.

A diode 39 and a capacitor 38 provide a power supply to enable the counter formed by units 15 and 16 to continue to operate in static conditions even during the 30 microsecond pause between two successive activation pulses belonging to the same train. The voltage at the terminals of capacitor 38 decreases during the intervals between two successive pulses of the same train, as a function of the leakage currents of the inversely polarized diode 39 and of the counter in question. Owing to the c-MOS nature of the circuit, its static consumption is so limited that the presence of a capacitor 38 of approximately 10 pF, fully compatible with the integration technology used for these circuits, is sufficient.

The constraint to be imposed on the discharge time of the capacitor 38, with allowance for the total leakage current present in the circuit or any leakage known and introduced a priori, must be such that the counter is kept active in the 30 microsecond pauses between successive activation impulses of a single train and at the same time it must be such as to ensure the switch-off of the circuit disposed in the tip 1 of the catheter, before the arrival of the next pulse train from the master control unit 9, which is at a time distance of approximately 3000 microseconds from the previous one, in order to ensure the resetting of the counter and the correct sequence of the transducers 2x-2y-2z with the first activation pulse of each train.

Figure 12:
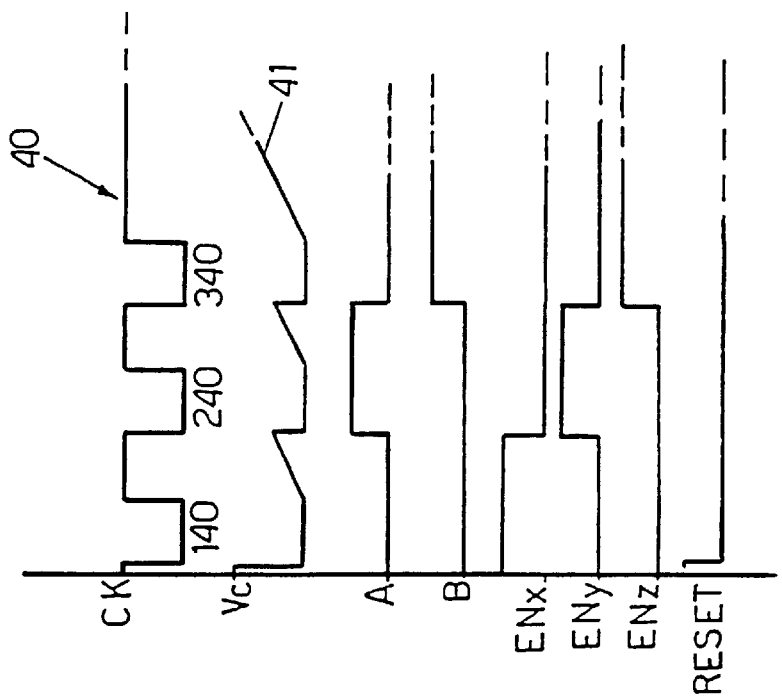
FIG. 12 shows the form of the output signals from some significant components of the circuit shown in FIG. 11.

FIG. 12 shows the waveforms relating to the circuit in FIG. 11, where 140-240-340 indicate the train of pulses spaced apart by 30 microseconds, which arrive at intervals of 3000 microseconds from the master control unit 9 to cause the successive switching of the switches 4x-4y-4z. The number 41 indicates the variation of the voltage Vc at the terminals of the capacitor 38.

The time constant 31 is of the order of a microsecond, permitting wide tolerances which do not adversely affect the operation of the instrument, this constant being used exclusively for the resetting of the timing circuit 210.

FIG. 13 shows the timing circuit 310 of the four-state circuit shown in FIG. 10, including components 33 and 34. The circuit shown in FIG. 13 differs from that in FIG. 11 in that the output of the logic circuit 35 determines the synchronisation pulse SYNC which controls the fourth state switch 34. The reset pulse for units 15 and 16 arrives from components 31 and 32 only if the capacitor 38 has previously been discharged; otherwise the counter restarts with ENx=1 after SYNC=1.

Figure 14:
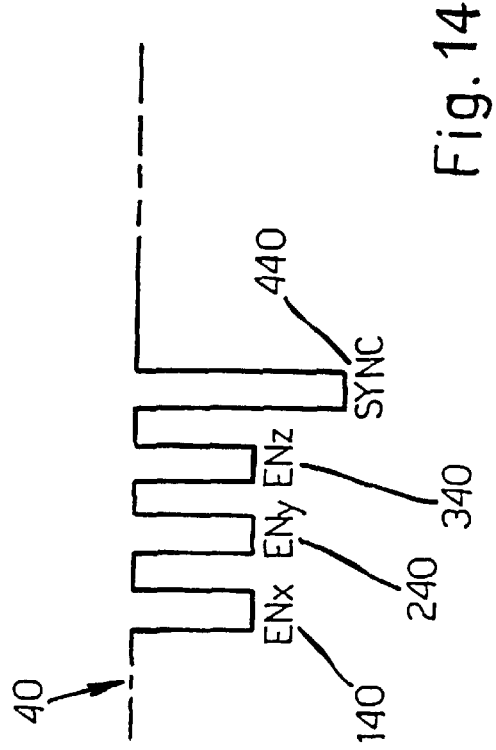
FIG. 14 shows the form of the cyclic activation signal of the device as shown in FIGS. 10 and 13.

The constraint to be imposed on the discharge time of the capacitor 38 of the circuit shown in FIG. 13 must be such that the counter is kept active in the 30 microsecond intervals, while there are no upper limits. With each activation pulse, the circuit switches and the capacitor 38 regains the charge lost during the pause. FIG. 14 shows how, after the final signal 340 of the pulse train 40 which causes the switching of the three acceleration transducers, the fourth state is activated, to provide at the output a signal 440 recognisable in amplitude by the master control unit 9 which will use it as the synchronisation signal to reset the correct transducer activation sequence whenever this is altered by any electrical or other interference.

FIG. 15 shows the possible configuration of the internal part of the master control unit 9 used for the reception and processing of the signal from the three uniaxial transducers disposed in the tip 1, to calculate the modulus or the mean of the peak-to-peak values of NHA read by the three transducers and relating to each cardiac cycle. The signals from the three transducers are amplified by a unit 43 and then sampled by means of corresponding sample and hold circuits 44-144-244 which are activated through the clock terminals 45-145-245 in phase with the activation of the said transducers by the unit 47 to which are connected the outputs of the devices 44-144-244 through corresponding band-pass filters 46-146-246 which operate in the band between approximately 15 and 100 Hz. The number 48 indicates the output of the unit 47 which sends the pulse train 40 to the tip of the catheter for the sequential activation of the three transducers. The signals from the three acceleration transducers, already with an upper band limit of 100 Hz, are reconstructed by an analog method, amplified and filtered in the 15–100 Hz band and collected by the unit 47 which uses analog or digital methods for the measurement of their peak-to-peak value and for subsequent processing in digital form to supply at its output 49 the modulus or the mean of the three peak-to-peak values of NHA measured in the three perpendicular directions by the three acceleration transducers. The said peak-to-peak values of the signals from the three acceleration transducers are read at the end of each cycle, and the means which control this reading in the unit 47 are automatically reset after each reading. The end of the cycle may be determined by interaction with known means which read a ventricular electrical stimulus or the QRS wave or a defibrillating electric shock, or may be determined autonomously by the said unit 47, after a programmed time interval, of the order of approximately 5 seconds for example.

By way of example, FIG. 16 shows the signals relating to the device shown in FIG. 15. The numbers 50-51-52 indicate the signals produced by the three acceleration transducers 2x-2y-2z, while 53 indicates the form of the signal which is cyclically emitted from the tip of the catheter and is sent to the master control unit 9. The numbers 54-55-56 indicate the signals emitted from the sample and hold circuits 44-144-244 relating to signals 50-51-52 respectively produced by the acceleration transducers.

Figure 17:
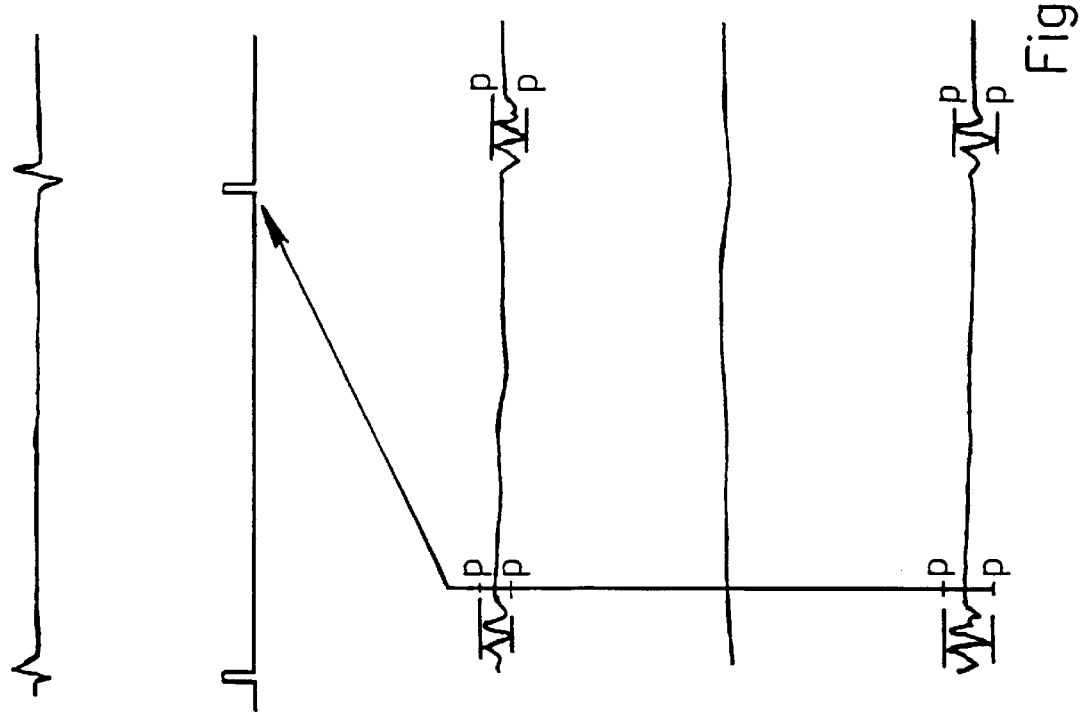
FIGS. 17 and 18 show the trend of the modulus of the peak-to-peak values of the NHA produced by the three uniaxial acceleration transducers used in the device shown in the preceding figures, in the transition from a rest situation to one of physical activity.
Figure 18:
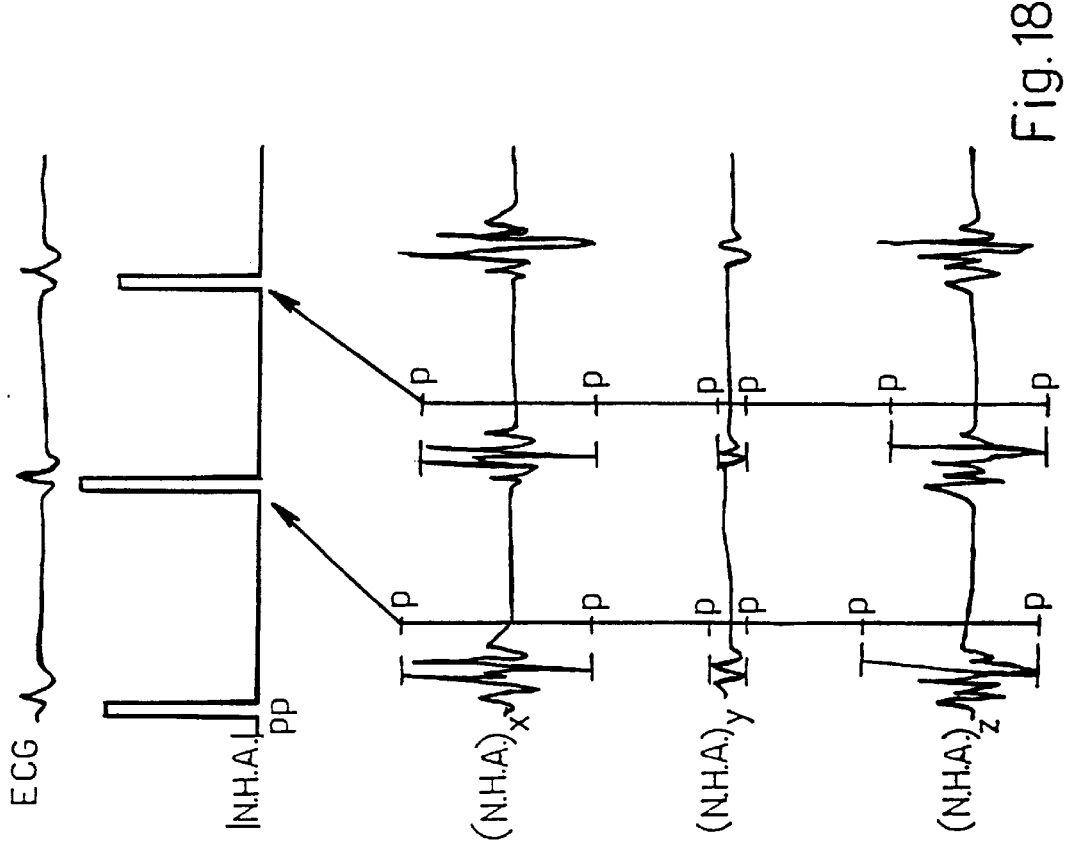

FIGS. 17 and 18 show the signals detected with the instrument according to the invention and relating to the modulus of the peak-to-peak values of NHA produced by the three transducers 2x-2y-2z in the resting state and in phases of physical activity respectively.

The disposition of the three acceleration transducers and of the electronic circuit associated with them inside the tip 1 of the catheter is illustrated in FIGS. 19-20-21. The reference number 57 indicates the catheter's sheath of insulating material which has good characteristics of biocompatibility and which terminates in a plurality of tines 58 to fix the tip of the said catheter to the heart tissue. The metal stimulating point 59, in the form of a capsule and made of material having good characteristics of biocompatibility, is fixed in the terminal part of the sheath 57 and operates in contact with the heart muscle. On the inner lateral surface of the point 59 are longitudinal recesses 60 in which are fitted the corner areas of a metal chassis 61 provided with at least one pair of longitudinal walls 161-261 spaced apart by an angle of 90° and with an end wall 361, perpendicular to the preceding walls on which are fixed the three uniaxial acceleration transducers 2x-2y-2z mentioned previously.

The acceleration transducers are fixed to the walls of the chassis 61 with the interposition between the two parts of an exact thickness 102 of a resilient conducting means, in order to mechanically reduce to approximately 100 Hz the upper limit of the frequency response of the transducers. The thickness of the said resilient conducting means may be formed by and coincide with the special transducer fixing adhesives according known techniques described for example in "Mechanical vibration and shock measurements" by Bruel & Kjaer.

The chassis 61 has a flat terminal part 461 aligned axially in the point 59 and with a forked end pressing on the metal plug 62 which is inserted in the inner end of the point 59 and is axially hollow for the passage of the negative electrode 8. The number 63 indicates the seal of ceramic material inserted in the plug 62 to form a grommet. The whole of the electronic circuit 64 to be linked with the acceleration transducers, as described previously with reference to the preceding figures, is mounted on the part 461 of the chassis. The positive electrode 7 is fixed, for example, to the plug 62 and consequently to all the metal parts housed in the point 59.

Figure 23:
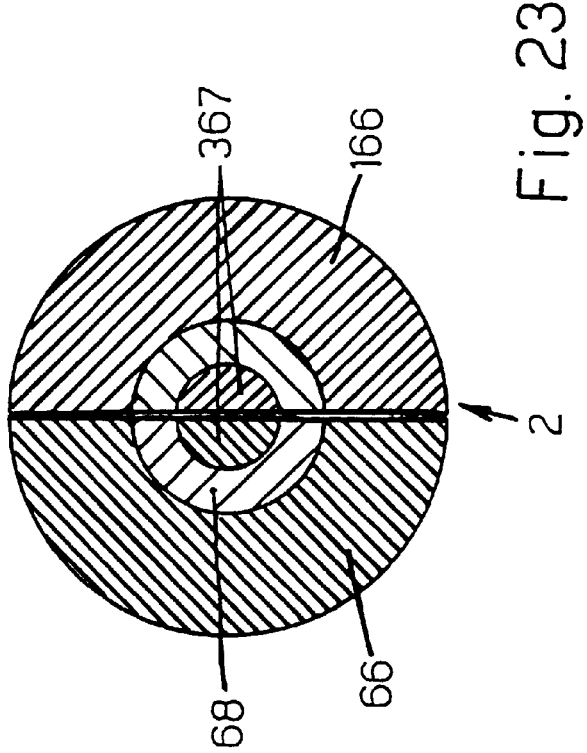
FIG. 23 is a side elevation of the transducer shown in FIG. 22, seen from the direction indicated by the arrow K.
Figure 22:
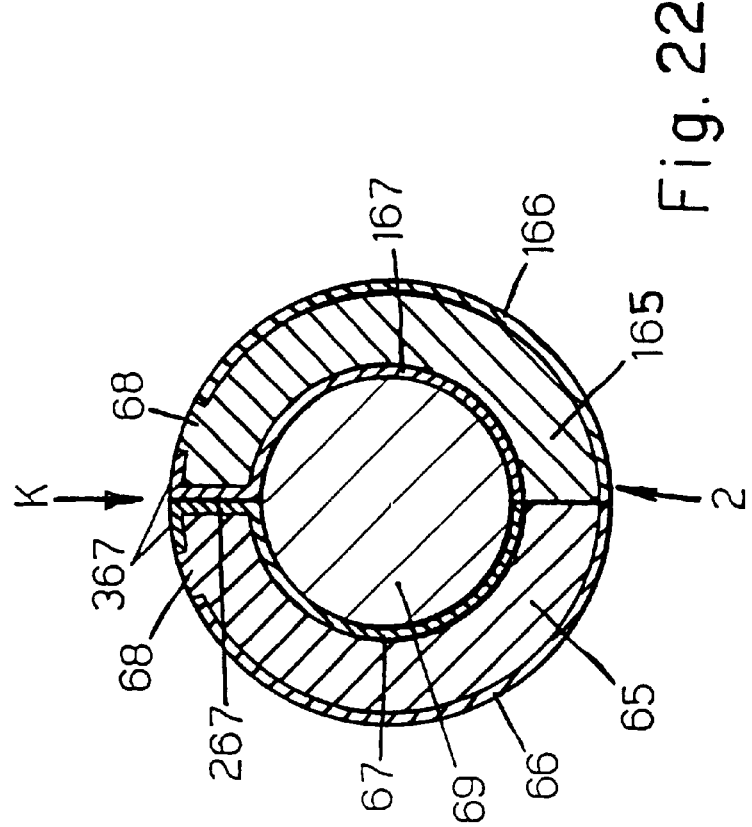
FIG. 22 shows a section through a multiaxial acceleration transducer of a new design particularly suitable for the purposes discussed herein.

With reference to FIGS. 22 and 23, a description will now be given of a rultiaxial transducer 2 which is particularly suitable for the purpose and which considerably simplifies the construction of the electronic circuit which is to be housed in the tip of the catheter. The transducer consists of two small hemispherical bodies 65-165 made of a suitable piezoelectric material, for example of the type shown in the catalogue "N.SG01E-4 transducer" Murata, Piezoelectric ceramics sphere type" and whose metal-coated parts are located on the outer and inner surfaces respectively as indicated by 66-166 and 67-167. By means of a metal extension 267 applied, for example, to one part of the superimposed edges of the bodies 65-165, the inner metal coating 67-167 is connected to a small metal isolated area 367 disposed on the outer face of the said bodies 65-165 and separated electrically from the coating 66-166 by a ring 68 of the material of the bodies 65-165.

The seismic mass 69 consisting of a metal sphere of suitable diameter is housed in the cavities formed by the hemispherical parts described. A small insert of sufficiently rigid anti-wear material, for example Parilene or Teflon, may be provided between the surface of the mass 69 and the metal coating 67-167.

Figure 25:
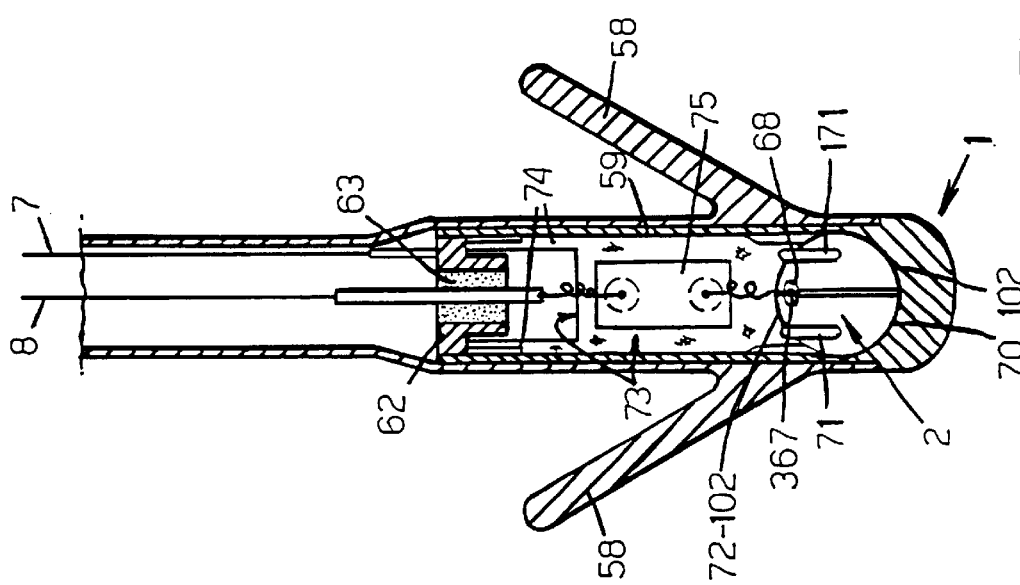
FIGS. 24 and 25 are longitudinal sections, viewed from two points separated by an angle of 90° through the point of a catheter containing within itself the multiaxial transducer illustrated in FIGS. 22 and 23.
Figure 24:
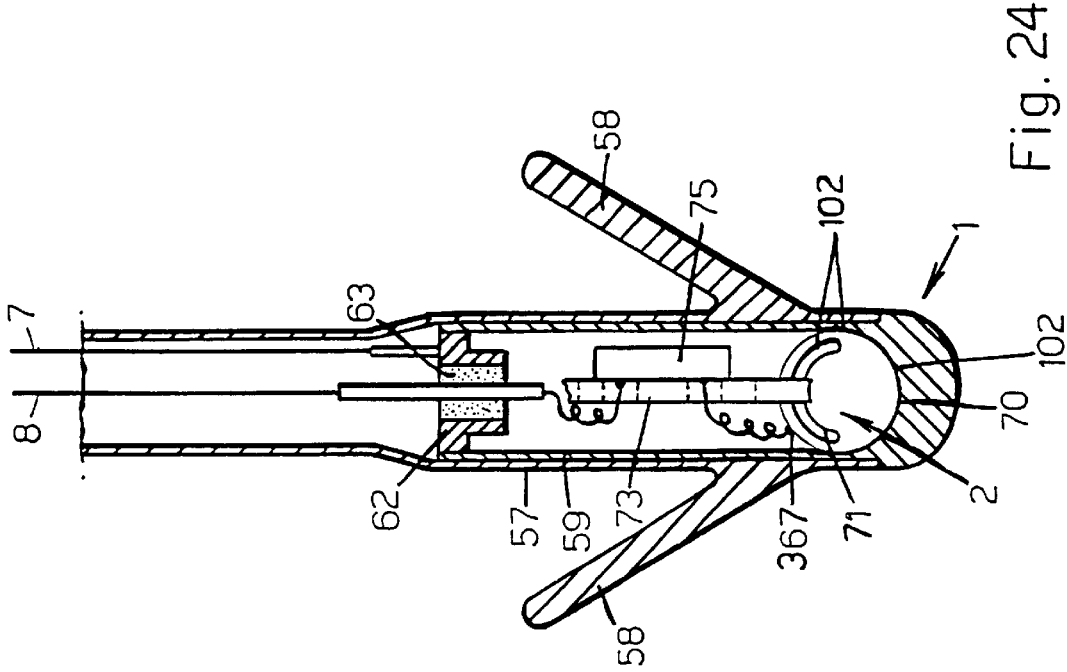

FIGS. 24 and 25 show that the spherical transducer 2 mentioned previously may be fixed, with the interposition of a layer 102 of resilient material having a thickness and elastic characteristics such that the top of the transducer band is limited to approximately 100 Hz, in a hemispherical socket 70 in the inner cavity of the metal point 59 of the catheter, in which it is retained by a pair of curved pieces 71-171 and by the curved end shape 72 of a small flat metal chassis 73 which terminates with its other forked end 74 pressing on the metal plug 62. An appropriate layer of the said material 102 having the function of limiting the top of the transducer band to approximately 100 Hz is also interposed in the area of contact between the transducer and the curved pieces 71-171 and the curved end 72 of the chassis 73.

It should be understood that, both in the case of the spherical transducer 2 and in the case of the three perpendicular transducers 2x-2y-2z, the reduction to approximately 100 Hz of the upper limit of the multiaxial transducer may be achieved by any means suitable for the purpose, used in combination with or as an alternative to the means 102 described. For example, it is possible for the multiaxial acceleration transducer, whether of the spherical type described above or of the preceding triaxial type, to be surrounded by a fluid or other means of specified viscosity, enabling the aforesaid results to be achieved.

Figure 26:
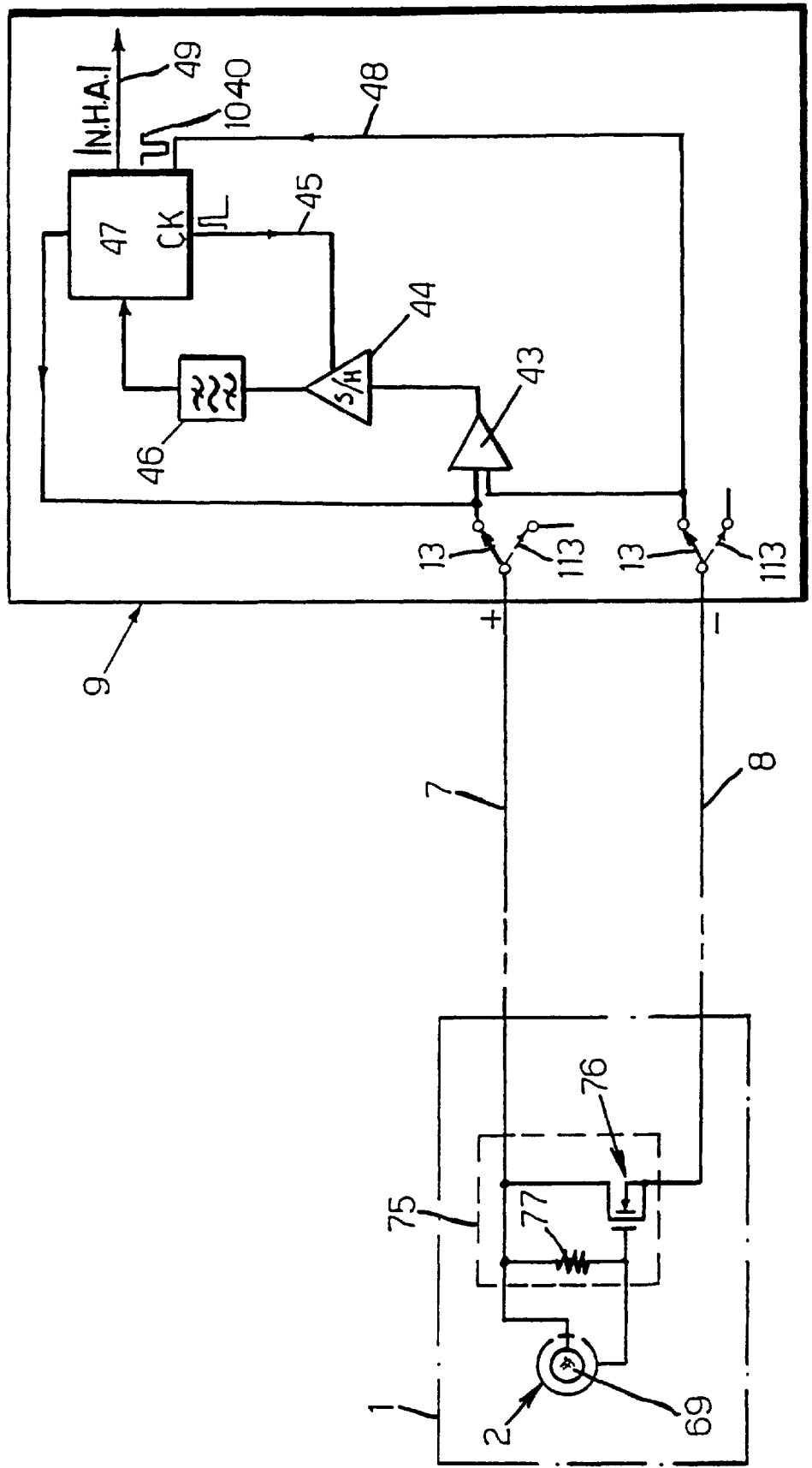
FIG. 26 shows the simple electronic circuit associated with the multiaxial transducer shown in FIGS. 20-21-22-23 and disposed partially in the catheter tip and partially in the master control unit.

The negative electrode 8 which passes through the ceramic seal 53 of the plug 52 is connected to the electronic circuit 75 fixed on the chassis 73 and associated with the spherical transducer 2. As shown in FIG. 26, the circuit 75 comprises a buffer made according to conventional methods with a MOS transistor 76 and a coupling resistor 77. The circuit 75 will be activated in a pulsed way and the modulus of the NHA measured by it will be transmitted through electrodes 7-8 to the subcutaneously implanted master control unit 9, in which it will be suitably amplified by the device 43, then reconstructed in analog mode by sampling by the sample and hold circuit 44, then filtered by the pass-band filter 46 to eliminate frequencies outside the band of approximately 15–100 Hz, and finally sent to the unit 47 which will supply at its output 49 the modulus or the mean of the peak-to-peak values of NHA measured in each cardiac cycle. The output 45 of the unit 47 triggers the clock of the sampling device 44, while the output 48 of the same unit 47 sends to the multiaxial transducer 2, disposed in the tip of the catheter, activation pulses 1040, having a duration of approximately 30 microseconds and sent at intervals of 3000 microseconds, with a consumption equal of course to one third of that of the preceding solution which uses a multiaxial acceleration transducer consisting of three uniaxial acceleration transducers.

The solution described in the present disclosure, namely that of mechanically limiting to 100 Hz the frequency response of the multiaxial acceleration transducer of the composite or simple type, enables the power consumption of the whole instrument to be limited. It should be understood, however, that if the instrument permits higher power consumption, for example in the case of the spherical type of acceleration transducer illustrated in FIGS. 22 to 26, the acceleration signal may be filtered in the 15–100 Hz band by an electronic method, without previous limitation of the band by the use of dampers 102 or in combination with such limitation. The signal generated by the multiaxial acceleration transducer is reconstructed in the master control unit 9 with a suitable sampling frequency, of the order of 1000 Hz for example, and the reconstructed signal is filtered in the 15–100 Hz band by the extraction of the part of the signal representing the cardiac contractility in the isovolumetric phase.

Any suitable acceleration transducer can be used. Known examples include torsional piezoresistive types in which a seismic mass introduces torsional stresses in a piezoresistive element which arrangement is inherently multiaxial; capacitive types in which for three dimensional operation three transducers are combined; and piezoresistive types in which for three dimensional operation three transducers are combined.

Finally, it should be understood that the scope of the invention includes the variant, not illustrated, in which the multiaxial acceleration transducer is fitted near the tip of the catheter, slightly to the rear, for example as in the case of the ring of a bipolar electrode. In this case the tip may be made with dimensions and a shape independent of those of the said multiaxial transducer and of the associated electronic circuit.

What is claimed is:

1. Apparatus for monitoring cardiac contractility, comprising a signal processing means and a catheter having a tip for insertion into the ventricle of the heart muscle, said catheter containing at or proximate its tip a first acceleration transducer responsive to the natural heart acceleration to provide an acceleration signal via said catheter to the signal processing means (9), characterized in that one of the signal processing means and the acceleration transducer is arranged to suppress frequencies outside the range of approximately 15 Hz to approximately 100 Hz.

2. Apparatus as claimed in claim 1, wherein the signal processing means is arranged to determine the peak of the acceleration signal.

3. Apparatus according to claim 1, characterized in that the acceleration transducer is located in the catheter with the interposition of a damping means (102) which reduces to approximately 100 Hz the upper limit of the response frequency of the acceleration transducer.

4. Apparatus according to claim 3, characterized in that the damping means (102) comprises resilient conducting material disposed between the transducer and a corresponding support.

5. Apparatus according to claim 4, in which the resilient conducting material comprises adhesives which fix the acceleration transducer to the corresponding support.

6. Apparatus according to claim 3, characterized in that the damping means (102) comprises an elastic and soft material which surrounds the acceleration transducer inside the catheter.

7. Apparatus according to claim 3, characterized in that the damping means (102) comprises a fluid which surrounds the acceleration transducer inside the catheter.

8. Apparatus as claimed in claim 1, characterized in that the acceleration transducer is responsive to acceleration in any spatial direction.

9. Apparatus as claimed in claim 8, wherein the acceleration transducer comprises three uniaxial acceleration transducers arranged with respective sensing axes on which they are sensitive perpendicular to each other, and wherein the signal processing means is arranged to determine the peak-to-peak value of the acceleration signal from each uniaxial transducer and to determine one of the modulus and the mean of the three peak-to peak signals.

10. Apparatus as claimed in claim 8, wherein the acceleration signal processing means calculates the modulus of the acceleration vector to which the sensor is subjected.

11. Apparatus as claimed in claim 10, in which the transducer (2) comprises a body of piezoelectric material in the form of a spherical casing formed by two hemispherical bodies (65-165) provided on inner and outer faces with corresponding inner and outer metal coatings, the inner metal coating being connected to an external contact (357) which forms an electrode of the transducer and which is electrically isolated from the rest of the outer metal coating which forms another electrode of the transducer, and a spherical seismic mass disposed inside the casing.

12. Apparatus according to claim 11, in which at least one layer of anti-wear material is provided between the seismic mass (69) and the inner metal coating (67-167).

13. Apparatus according to claim 11, in which the casing of the transducer (2) is housed in a terminal socket (70) of a hollow metal point (59) of the tip of the catheter, and the transducer has its isolated electrode (367) gripped and retained in situ by a forked end (71-171-72) of a flat metal chassis (73) disposed longitudinally in the point and carrying an electronic circuit (75) associated with the transducer, another end of said chassis pressing on a hollow metal plug (62) fixed within the hollow point (59), and said plug including an internal grommet (63) through which passes the electrode (8) connected to the electronic circuit, said another electrode (7) being connected to the plug.

14. Apparatus according to claim 13 in which the electronic circuit (75) comprises a buffer consisting of a MOS transistor (77) and a corresponding coupling resistor (77).

15. Apparatus according to any claim 1, including means for sampling the output of the acceleration transducer periodically to provide a sampled acceleration signal; and wherein the signal processing means includes means for reconstructing a continuous acceleration signal from the sampled acceleration signal; and a band pass filter having a pass band of approximately 15 Hz to approximately 100 Hz for filtering the reconstructed acceleration signal.

16. Apparatus according to claim 15, characterized by mechanical damping means (102) disposed on the acceleration transducer to limit the top of the band to approximately 100 Hz.

17. Apparatus according to claim 16 characterized in that the acceleration transducer is responsive to acceleration in any spatial direction, and wherein the signal processing means (9) comprises:

means to send current pulses to activate the acceleration transducer (2), said pulses having a duration of approximately 30 microseconds at intervals of approximately 3000 microseconds; and means (47) for determining the peak-to-peak values of the filtered signal and for processing the filtered signal to calculate the value of cardiac contractility in successive heart cycles.

18. Apparatus as claimed in claim 17, including means for detecting, for determining the end of each heart cycle, any of a ventricular electrical stimulus, a QRS wave, an electric defibrillation shock, and a programmed time interval of the order of approximately 5 seconds.

19. Apparatus according to claim 17, wherein the acceleration transducer comprises three uniaxial acceleration transducers and including a chassis (61) fixed inside a hollow metal point (59) of the tip of the catheter, the chassis including a section having at least two longitudinal walls (161-261) perpendicular to each other and an end wall (361) perpendicular to the two walls, the uniaxial acceleration transducers being fitted on respective said walls with the interposition of the damping means (102), the chassis being provided with a flat terminal section (461) disposed coaxially in the hollow point of the catheter and having a forked end pressing on a metal plug (62) fixed within the point, the metal plug carrying a grommet (63) through which passes an electrode (8) which is connected to an electronic circuit (64) associated with the acceleration transducers and fixed to the flat terminal section of the chassis (61), and another electrode (7) being electrically connected to the metal plug.

20. Apparatus according to claim 12 in which the acceleration transducer (2) comprises three uniaxial acceleration transducers (2x-2y-2z) arranged with the respective sensing axes on which they are sensitive perpendicular to each other, the transducers having respective buffers (11-111-211) connected through corresponding transducer switches (4x-4y-4z) to an input of an output buffer (5), a timing circuit (10) controlling the switches so that the signals produced by the three acceleration transducers are available in separate and successive time intervals, and said output buffer providing a supply voltage for said timing circuit.

21. Apparatus as claimed in claim 20, wherein one of the sensing axes is aligned with the axis of the tip (1) of the catheter.

22. Apparatus according to claim 20, in which means are provided to activate the timing circuit (10) when it receives from the signal processing means (9) a pulse (14) of the order of a few tens of microamperes, maintained for a total time interval (T) of the order of approximately a hundred microseconds.

23. Apparatus according to claim 20, in which the timing circuit (10) comprises a counter (15-16) having outputs (17-18-19) to control the transducer switches (4x-4y-4z), means (32) for resetting the counter on arrival of an activation signal (14) from the signal processing means (9), the timing circuit including clock means (20-21-22-23-24-25-26-27-28-29) for applying to the counter a switching clock pulse of approximately 30 microseconds, and means (29-30) to de-activate or disable said clock means when the counter reaches a predetermined count.

24. Apparatus according to claim 20, in which the input to the output buffer (5) is connectable through a load switch (34) to a load (33), the timing circuit (110) comprising a counter (15-16) having outputs which control said transducer switches and said load switch so that operation of said load switch produces a distinctive end-of-reading voltage signal at the output of the output buffer (5), the signal processing means (9) being responsive to said end-of-reading signal to interrupt the supply to the whole circuit located in the catheter.

25. Apparatus according to claim 24 wherein the signal processing means is responsive to said end-of-reading signal for generating a voltage which saturates a current generator supplying current to said circuit.

26. Apparatus according to claim 24, characterized in that the timing circuit (110) associates an end-of-reading state with each said separate and successive time interval means being provided in the signal processing means (9) to make the unit read the individual transducers in real time.

27. Apparatus according to claim 24, characterized in that the timing circuit (310) is responsive to a pulse train (40) from the signal processing means (9) to sequentially trigger the transducer switches (4x-4y-4z) and the load switch (34), said pulse train having a cyclic repetition every 3000 microseconds, and each pulse of the train lasting for approximately 30 microseconds and being separated from the next pulse by approximately 30 microseconds; the timing circuit (310) including means (36,37) responsive to the counter reaching a full count to reset the counter after a time delay (31) of the order of a microsecond, and a capacitor (38) supplying power to the counter for keeping the counter active for at least 30 microseconds.

28. Apparatus according to claim 20, characterized in that the signal processing means (9) provides successive trains of current pulses at cyclic intervals and in which each pulse in the train is separated from the next pulse, the timing circuit comprising a counter (15-16) arranged to count the pulses in said pulse trains, and having four outputs (17-18-19-35), in which the first three outputs control the switches of the acceleration transducers (2x-2y-2z) and the fourth output (35) is connected through a delay line (37) and a logic circuit (36 to reset the counter, resetting of the counter also being provided through a suitable time constant (31) at the start of the cycle, a capacitor (38) providing power to the timing circuit to keep the counter active between pulses in the trains, and the capacitor being included within an electrical circuit providing a rate of discharge of the capacitor such that the capacitor is discharged in a time interval less than that between the pulse trains (40) from the signal processing means.

29. Apparatus according to claim 20, characterized in that the signal processing means (9) includes means (44-144-244) to reconstruct continuous acceleration signals relating to the three acceleration transducers (2x-2y-2z), and passband filters (46-146-246) to filter the reconstructed signals, in the pass band of approximately 15–100 Hz, the three signals thus obtained being processed by means (47) which determine their peak-to-peak value and then determines one of the modulus and the mean of the three peak-to-peak values.

\* \* \* \* \*